United States Patent [19]

Adam

[11] 4,061,751

[45] Dec. 6, 1977

[54] 6-SUBSTITUTED 3-NITROIMIDAZO[1,2-b]PYRIDAZINE FOR THE CONTROL OF FOOT ROT AND LIVER LESIONS IN RUMINANT ANIMALS

[75] Inventor: Alberto Eilert Adam, Wayne, N.J.

[73] Assignee: American Cyanamid Company, Stamford, Conn.

[21] Appl. No.: 707,921

[22] Filed: July 22, 1976

[51] Int. Cl.$^2$ .................... A61K 31/50; A61K 31/54; A61K 31/535

[52] U.S. Cl. .................................... 424/250; 424/246; 424/248.4

[58] Field of Search ....................... 424/250, 248, 246

[56] References Cited

U.S. PATENT DOCUMENTS

| 3,711,613 | 1/1973 | Tomcufcik etal. .................. 424/250 |
| 3,725,407 | 4/1973 | Tomcufcik et al. ................. 424/250 |

*Primary Examiner*—Sam Rosen
*Attorney, Agent, or Firm*—H. G. Jackson

[57] ABSTRACT

This disclosure describes compositions of matter useful for the treatment and prophylaxis of foot rot and liver lesions in ruminant animals. It also describes methods for controlling and preventing foot rot and liver lesions in ruminant animals, by administering to the animals an effective amount of a 6-substituted 3-nitroimidazo[1,2-b]pyridazine.

7 Claims, No Drawings

6-SUBSTITUTED 3-NITROIMIDAZO[1,2-B]PYRIDAZINE FOR THE CONTROL OF FOOT ROT AND LIVER LESIONS IN RUMINANT ANIMALS

BRIEF SUMMARY OF THE INVENTION

This invention relates to novel compositions of matter useful in the veterinary field for the treatment and prophylaxis of foot rot and liver lesions in ruminant animals, particularly in cattle, sheep and goats. The invention also relates to therapeutic and prophylactic compositions containing a 6-substituted 3-nitroimidazo[1,2-b]pyridazine which are useful for the control or prevention of foot rot and liver lesions in ruminant animals.

BACKGROUND OF THE INVENTION

The compounds of the present invention are described in the A. S. Tomcufcik et al. U.S. Pat. Nos. 3,725,407 issued Apr. 3, 1973; 3,828,041 issued Aug. 6, 1974 and 3,905,974 issued Sept. 16, 1975. The patentees describe methods for synthesizing 6-substituted 3-nitroimidazo[1,2-b]pyridazines and indicate that the compounds can be used to control amoebic and trichomonal infections in warm-blooded animals. No suggestion is made and it is not obvious from the disclosure that the stated compounds would be effective for the control of foot rot and liver abscesses in ruminant animals.

DETAILED DESCRIPTION

Diseases which debilitate vast numbers of animals each year and are responsible for significant economic losses to those in ruminant husbandry, are necrobacillosis, foot rot and liver abscesses. The causative agents for these diseases are anerobic bacteria. *Fusobacterium necrophorum* also referred to as *Fusoformis necrophorus*, has been isolated from cases of foot rot, liver abscesses and various other lesions. The organism is widespread in nature and apparently proliferates rapidly at the cites of wounds in animals and/or on the skin or mucous membrane of animals with lowered resistance.

Foot rot is a contagious disease which occurs in the feet of sheep and goats. It is characterized by separation of a large portion of the hoof from the soft tissues due to spreading infection beneath the horn. Severe pain accompanies the disease which is widespread in most countries wherein sheep and goats are raised in large numbers. Treatments for the disease have generally involved topical applications of disinfectants, chemotherapeutic agents and/or antibiotics. Among the disinfectants which have been employed in this manner are tincture of chloramphenicol, 10% formalin solution and 15% picric acid in alcohol. Antibiotics and chemotherapeutic agents that have been utilized with some success in the treatment of foot rot and skin lesions include the tetracycline antibiotics and selected sulphonamides. Such treatments have not, however, provided entirely satisfactory control of the above-mentioned diseases. It is an object of this invention to provide a method for the prevention and/or cure of foot rot and liver lesions in ruminant animals by administering thereto a prophylactic and/or therapeutic amount of a 6-substituted 3-nitroimidazo[1,2-b]pyridazine having the structure described below. It is also an object of this invention to provide a method for controlling pathogenic anerobic organisms in homothermic animals by orally administering to the animals an effective amount of a 6-substituted 3-nitroimidazo[1,2-b]pyridazine, as described below.

In accordance with this invention we have found a method for controlling foot rot and liver lesions in ruminant animals by orally administering to the host an effective amount (prophylactic or therapeutic) of a compound having the formula:

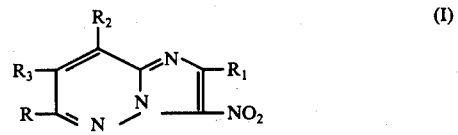

wherein R is hydroxy, mercapto, alkoxy ($C_1$–$C_8$) alkylthio ($C_1$–$C_8$), phthalimidoloweralkoxy, phenylloweralkoxy, lower alkylaminoloweralkoxy, lower alkoxyloweralkoxy, hydroxyloweralkoxy, lower alkenyloxy, halobenzoylloweralkoxy, amino, alkyl ($C_1$–$C_8$) amino, dialkyl ($C_1$–$C_8$) amino, di(hydroxyloweralkyl) amino, hydroxyloweralkylamino, lower alkoxyloweralkylamino, lower alkenylamino, phenylloweralkylamino, pyridylloweralkylamino, cycloalkyl ($C_3$–$C_6$) amino, diloweralkylaminoloweralkylamino, 1-piperidinyl, 1-pyrrolidinyl, 4-loweralkyl-1-piperazinyl, 4-lower alkoxyphenyl-1-piperazinyl, morpholino, imidazolyl, 4-carboloweralkoxy-1-piperazinyl 4-diloweraminoloweralkyl-1-piperazinyl, sulanilamido, alkyl ($C_1$–$C_4$) sulfanilamido, 3-nitro-4-chlorobenzamido, thiomorpholino-S,S-dioxide, p-chlorobenzoylhydrazido, p-chlorobenzylidene hydrazino, nicotinylidene hydrazino, loweralkylthioloweralkoxy, loweralkylsulfonylloweralkoxy or —$NR_4$—CO—$R_5$ where $R_4$ is hydrogen, or alkyl $C_1$–$C_4$ and $R_5$ is alkyl $C_1$–$C_{11}$, phenyl, 4-chloro-3-nitrophenyl, benzyl, mono and dihaloalkyl ($C_1$–$C_4$) or 2-phenoxypropionamide; $R_1$ is hydrogen or alkyl $C_1$–$C_4$; $R_2$ and $R_3$ are hydrogen or methyl; and the pharmaceutically acceptable acid addition salts thereof.

A preferred group of compounds useful in the practice of the method of this invention have the formula:

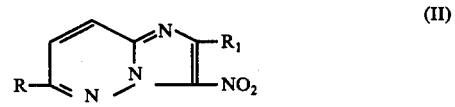

wherein R is hydroxy, mercapto, alkoxy ($C_1$–$C_8$) alkylthio ($C_1$–$C_8$), phthalimidoloweralkoxy, phenylloweralkoxy, lower alkylaminoloweralkoxy, lower alkoxyloweralkoxy, hydroxyloweralkoxy, lower alkenyloxy, halobenzoylloweralkoxy, amino, alkyl ($C_1$–$C_8$) amino, dialkyl ($C_1$–$C_8$) amino, di(hydroxyloweralkyl)amino hydroxyloweralkylamino, lower alkoxyloweralkylamino, lower alkenylamino, phenylloweralkylamino, pyridylloweralkylamino, cycloalkyl ($C_3$–$C_6$) amino, diloweralkylaminoloweralkylamino, 1-piperidinyl, 1-pyrrolidinyl, 4-loweralkyl-1-piperazinyl, 4-lower alkoxyphenyl-1-piperazinyl, morpholino, imidazolyl, 4-carboloweralkoxy-1-piperazinyl or 4-diloweraminoloweralkyl-1-piperazinyl, loweralkylthioloweralkoxy, loweralkylsulfonylloweralkoxy, $R_1$ is hydrogen or loweralkyl and a pharmaceutically acceptable acid addition salt thereof.

Another preferred group of compound useful in the practice of this invention may be represented by the formula:

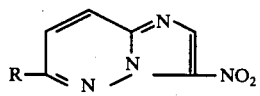
(III)

wherein R is sulfaniliamido; alkyl ($C_1-C_4$) sulfanilamido; 3-nitro-4-chlorobenzamido; thiomorpholino-S,S-dioxide; p-chlorobenzoyl hydrazido; p-chlorobenzylidene hydrazino; nicotinylidene hydrazino or $-NR_4-CO-R_5$ where $R_4$ is hydrogen or alkyl $C_1-C_4$ and $R_5$ is alkyl $C_1-C_{11}$, phenyl, 4-chloro-3-nitrophenyl, benzyl, mono or dihaloalkyl $C_1-C_4$, or 2-phenoxypropionamide; and the pharmaceutically acceptable acid addition salts thereof.

Especially preferred compounds useful in this invention can be further defined as follows: (1) Formula II compounds wherein $R_1$ is hydrogen and R is 4-loweralkyl-1-piperazinyl, amino, alkoxy ($C_1-C_8$), diloweralkylaminoloweralkylamino, hydroxyloweralkylamino or imidazolyl; and (2) Formula III compounds where R is $-NR_4-CO-R_5$, $R_4$ is hydrogen or methyl and $R_5$ is alkyl $C_1-C_{11}$, phenyl 4-chloro-3-nitrophenyl, benzyl, dichloromethyl or 2-phenoxypropionamide; and the pharmaceutically acceptable salts of both of the above defined formula II and III compounds.

Formula III compounds wherein R is sulfanilamido; alkyl ($C_1-C_4$) sulfanilamido; 3-nitro-4-chlorobenzamido; thiomorpholino-S,S-dioxide; p-chlorobenzoylhydrazido; p-chlorobenzylidene hydrazino; nicotinylidene hydrazino or $-NR_4-CO-R_5$ where $R_4$ is H or methyl and $R_5$ is phenyl, 4-chloro-3-nitrophenyl, benzyl, dichloromethyl or 2-phenoxypropionamide, can be prepared in accordance with the Tomcufcik et al. procedures U.S. Pat. No. 3,725,407 using the appropriate reactants. The procedure may be graphically illustrated as follows:

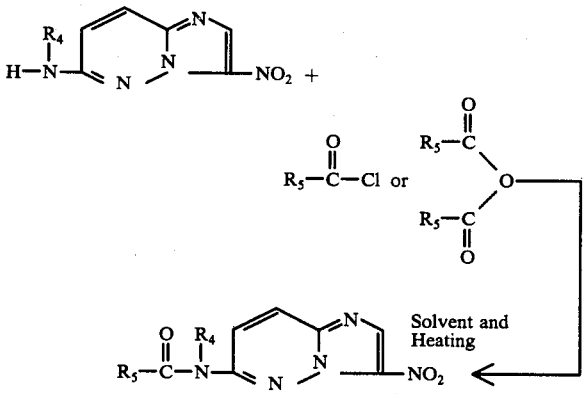

wherein $R_4$ and $R_5$ are as defined immediately above. These reactions are conducted under the conditions described by Tomcufcik et al.

I have found that a 6-substituted 3-nitroimidazo[1,2-b]pyridazine, as described above, is effective for the control of foot rot and liver abscess in ruminants when orally administered to infected host animals in amounts ranging from about 3.0 mg to about 100 mg per kilogram of body weight per day. A preferred dosage regimen for optimum results would be from about 10 mg to about 50 mg orally per kg of body weight per day. Such dosage units are employed that a total of from about 50 mg (for a 16 kg animal at 3.0 mg/kg) to about 10.0 grams (for a 100 kg animal at 100 mg/kg) of active ingredient are administered orally in a 24-hour period. The daily dosage may be administered as a single oral dose or as divided doses depending upon the exigencies of the therapeutic situation.

The dosage units of active compound may contain other inert or medically active materials, for instance, when the dosage unit form is a tablet, pill or granules, there may also be present various binders, fillers or solid diluents. Suitable materials for this purpose may be for example, starch such as corn starch, or sugar as lactose or sucrose. When the dosage unit form is a capsule, it may contain in addition to materials of the above type a liquid carrier such as a fatty oil. The dosage unit form may also have present excipients such as dicalcium phosphate. Various other materials may be present as coatings or to otherwise modify the physical form of the dosage unit, for instance, pills or capsules may be coated with shellac, sugar or both. Of course, any material used in preparing the dosage unit form should be pharmaceutically pure and substantially nontoxic in the amounts employed.

Where the drug is to be administered as a single oral dose, for example in a therapeutic treatment, 5.25% by weight of the drug may be mixed with 4.25% by weight of hydroxystearin and 90.50% by weight of sesame oil. This formulation is administered by a syringe as an oral paste and will provide about 250 mg of drug per cubic centimeters (cc). It is, of course, obvious that a higher concentration of the drug can be achieved by altering the quantities of drug and sesame oil accordingly.

For phophylactic administration, the active ingredient is preferably administered either in the feed or in the drinking water at levels of from about 25 to about 500 parts per million, and preferably at levels of from 50 to 250 parts per million. This treatment is usually effective when administered over about a one-day to two-week period, although the treatment period may be extended if so desired. For prophylactic or therapeutic treatment of animal via feed treatment, any conventional animal feed may be employed.

As indicated above, the 6-substituted 3-nitroimidazo[1,2-b]pyridazine is normally administered to the animals intimately mixed in the feed ration or drinking water for prophylaxis. The drug can be suitably prepared as a premix or feed supplement containing from about 1% to about 90% by weight of the formulation which can also contain various diluents or carriers. Carriers suitable for use to make up the feed supplement compositions include the following: soybean meal, alfalfa meal, cotton seed oil meal, linseed oil meal, cornmeal, cane molasses, urea, bone meal, corncob meal, dried fermentation whole mash solids, and the like. The carrier promotes a uniform distribution of the drug in the finished feed with which the supplement is blended. It thus performs an important function by ensuring proper distribution of the drug throughout the feed. The feed supplement or premix containing the active ingredient can be readily mixed with the feed ration by any conventional technique for mixing feeds. For convenience in commercial use, it has been found that premixes containing from about 5% to about 15% by weight of the active compound are preferred. When administering the compound in drinking water, it has been found convenient to utilize water-soluble excipients, e.g., lactose, dextrose, tartaric acid. The powder can be added to drinking water to provide an effective concentration level of active compound of from about 0.0025% to about 0.05% by weight.

Also in accordance with this invention, we have found that the above-identified ruminant foot rot and liver abscess control agents can be used in combination with other drugs, such as anti-bacterial agents, antifungal agents, growth promoting agents, and the like, normally used in the raising of the animals.

For a clearer understanding of this invention, specific examples of it are set forth below. These examples are merely illustrative, and are not to be understood as limiting the scope and underlying principles of the invention in any way.

EXAMPLE 1

Procedure for determining in-vitro activity against *Fusobacterium necrophorum* is as follows:

1. Inoculum: Inoculum of *F. necrophorum* is prepared by adding 0.8 ml of an overnight PRAS broth culture to 9.0 ml of dilution fluid.

2. Compounds: Compounds are sonicated in sterile distilled water and diluted to contain 500 mcg/ml. Paper disc, calibrated to absorb 0.02 ml are saturated with drug solution. Each disc contains 10 mcg of compound.

3. Procedure: Anaerobic blood agar plates are streaked in three directions with inoculum absorbed on a sterile cotton swab. Duplicate discs are placed on the seeded agar. Plates are incubated at 37° C. in GasPacks (Baltimore Biological Laboratory, Md.) containing a fresh catalyst and $CO_2$ + $H_2$ generator envelope. After 48 hr. incubation plates are examined for zones of inhibition. Active compounds are rated +, inactive compounds are given a − rating. Data obtained are reported in Table I below. The above-identified organism *Fusobacterium necrophorum* has been identified, by researchers investigating the causative agent for foot rot in sheep and goats and for liver abscesses in cattle. Data obtained are reported in Tables I and II below.

TABLE I

Control of *Fusobacterium necrophorum* with 6-substituted 3-nitroimidazo[1,2-b]pyridazines having the formula:

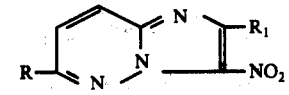

| R | $R_1$ | Control of *F. necrophorum* |
|---|---|---|
| —OCH₃ | H | + |
| —N(CH₃)₂ | H | + |
| —OC₂H₅ | H | + |
| | H | + |
| —N(piperazine)N—CH₃ | | |
| —OCH₃ | CH₃ | + |
| —NHCH₃ | H | + |
| —NH₂ | H | + |
| Cl | CH₃ | + |
| —N(CH₃)₂ | CH₃ | − |
| H | H | + |
| —NHCOCH₃ | H | + |
| —N(C₄H₉)₂ | H | + |
| —N(morpholino)O | | |
| —N(CH₃)—CH₂—C₆H₅ | H | + |
| —N(CH₂—CH₂—OH)₂ | H | + |

TABLE I-continued

Control of *Fusobacterium necrophorum* with 6-substituted 3-nitroimidazo[1,2-b]pyridazines having the formula:

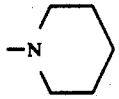

| R | $R_1$ | Control of *F. necrophorum* |
|---|---|---|
| —NH—CH₂CH=CH₂ | H | + |
| —N(piperidino) | H | + |
| —N(CH₃)(C₂H₅) | H | + |
| —N(CH₃)(C₄H₉) | H | + |
| —N(piperazine)N—CO₂C₂H₅ | H | + |
| —NH(CH₂)₂—N(C₂H₅)₂ . HCl | H | + |
| —NH(CH₂)₃N(CH₃)₂ | H | + |
| —NH—CH₂-(pyridyl) | H | + |
| —NHC₈H₁₇ | H | + |
| —NH—NH—CO-(C₆H₄)-Cl | H | + |
| —N⁺(CH₃)₃O₃⁻S-(C₆H₄)-CH₃ | H | + |
| —N(piperazine)N—(CH₂)₃—N(CH₃)₂ . 2HCl | H | + |
| —OC₄H₉ | H | + |
| —N(CH₃)—C₈H₁₇ . HCl | H | + |
| —OCH₂C₆H₅ | H | + |
| | CH₃ | + |
| | H | − |
| -(dichlorophenyl) | | |
| —NH—CH(C₂H₅)—CH₂—OH | H | + |
| —N(imidazolyl) | H | + |
| | H | − |
| —NH—N=CH-(C₆H₄)-Cl | | |
| —NH—CO—C₆H₅ | H | + |
| —OCH₂—COOC₂H₅ | H | + |
| —NH—N=C-(pyridyl) | H | + |

TABLE I-continued

Control of *Fusobacterium necrophorum* with 6-substituted 3-nitroimidazo[1,2-b]pyridazines having the formula:

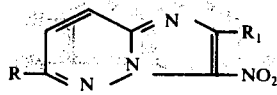

| R | $R_1$ | Control of *F. necrophorum* |
|---|---|---|
| —N(CH₃)—COCH₃ | H | + |
| —OCH₂CH=CH₂ | H | + |
| —OCH₂—CO—C₆H₄—Cl | H | + |
| —H—CO—C₂H₅ | H | + |
| —OCH₂CH₂—OC₂H₅ | H | + |
| —OCH(CH₃)₂ | H | + |
| —OC₃H₇ | H | + |
| —OCH₂CH₂OH | H | + |
| —OC₈H₁₇ | H | + |
| —OCH₂CH₂—N(phthalimido) | H | + |
| —N(morpholinyl-SO₂) | H | + |
| —NH—CO—CH₂—C₆H₅ | H | + |
| —NH—CO—C₁₁H₂₃ | H | + |
| —NH—CO—CHCl₂ | H | + |
| —N(piperazinyl-NH) | H | + |
| —NH—CO—CH(CH₃)—O—C₆H₅ | H | + |
| —NH—SO₂—CH₃ | H | + |
| —NH—SO₂—C₆H₄—NH₂ | H | + |
| —OCH₂CH₂—O—CH₃ | H | + |
| —OCH₂CH₂—S—C₂H₅ | H | + |
| —OCH₂—CH₂—SO₂—C₂H₅ | H | + |
| —N(thiomorpholinyl-SO₂) | H | + |
| —C₆H₃Cl₂ | H | + |
| —NH—SO₂—CH₃ | H | + |
| —N(pyrrolidinyl) | H | + |
| OCH₂CH₂N(CH₃)₂ · HCl | H | + |
| NH—CH₂C₆H₅ | H | + |
| —NH—NH—CO—C₆H₄—Cl | H | + |

Table II

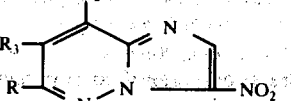

| R | $R_2$ | $R_3$ | Control of *F. necrophorum* |
|---|---|---|---|
| Cl | CH₃ | H | + |
| Cl | H | CH₃ | + |
| OCH₃ | CH₃ | H | + |
| OCH₃ | H | CH₃ | + |

EXANPLE 2

Procedure for determining activity against a *Fusobacterium necrophorum* infection in mice is as follows:

1. Inoculum: *F. necrophorum* (ATCC 27852) is maintained in prereduced anaerobically sterilized (PRAS) chopped meat carbohydrate broth at room temperature. Inoculum is prepared from an overnight PRAS brain heart infusion supplemented broth culture incubated at 37° C. The culture is centrifuged, the supernatant discarded and cells resuspended in dilution fluid to contain approximately $5 \times 10^7$ cells/ml. All bacteriological procedures are carried out under deoxygenated carbon dioxide using an anerobic station (Kontes, Vineland, N.J.). Mice are inoculated intraperitoneally with 0.2 ml of diluted culture averaging $10^4$ cells/mouse.

2. Mice: Eighteen to twenty gm CF-1 female mice are purchased from Carworth, Division of Charles River Breeding Laboratories, Inc. (Wilmington, MA).

3. Procedure: Drug diet is prepared by mixing 200 mg of compound in 500 mg of Purina Mouse Meal yielding compound at 400 ppm. Mice are weighed and fed drug diet ad libitum beginning two days before being inoculated with *F. necrophorum*. The day of challenge mice and feed are weighed and feed consumption calculated. Mortality is recorded daily and the experiment is terminated 14 days after challenge. Statistical significance of survival is calculated using the four-fold contingency test of D. Mainland and I. M. Murray (Science, 116 page 591–594, 1952). Compounds found to be effective for controlling *Fusobacterium necrophorum* infections in mice are rated +; those found to be ineffective are rated —. Data obtained are reported in Table III below.

Table III

Control of *Fusobacterium necrophorum* in mice using a 6-substituted 3-nitroimidazo[1,2-*b*]pyridazine havong the formula:

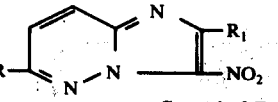

| R | $R_1$ | Control of *F. necrophorum* in Mice |
|---|---|---|
| —N(CH₃)₂ | H | + |
| —NHCH₂CH=CH₂ | H | + |
| —OCH₂CH₂OC₂H₅ | H | + |
| —OC₃H₇ | H | + |
| H | H | — (IP) |
| —N(pyrrolidinyl) | H | — (IP) |

(IP) = Drug administered by interperitoneal injection.

I claim:

1. A method of treating foot rot and liver abscesses in ruminant animals which comprises, administering to the animals a therapeutically effective amount of a compound having the formula:

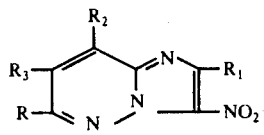

wherein R is hydroxy, mercapto, alkoxy ($C_1$-$C_8$), alkylthio ($C_1$-$C_8$), phthalimidoloweralkoxy, phenylloweralkoxy, lower alkylaminoloweralkoxy, lower alkoxyloweralkoxy, hydroxyloweralkoxy, lower alkenyloxy, halobenzoylloweralkoxy, amino, alkyl ($C_1$-$C_8$) amino, dialkyl ($C_1$-$C_8$) amino, di(hydroxyloweralkyl)amino, hydroxyloweralkylamino, lower alkoxyloweralkylamino, lower alkenylamino, phenylloweralkylamino, pyridylloweralkylamino, cycloalkyl ($C_3$-$C_6$) amino, diloweralkylaminoloweralkylamino, 1-piperidinyl, 1-pyrrolidinyl, 4-loweralkyl-1-piperazinyl, 4-lower alkoxyphenyl-1-piperazinyl, morpholino, imidazolyl, 4-carboloweralkoxy-1piperazinyl or 4-diloweraminoloweralkyl-1-piperazinyl, sulfanilamido, alkyl ($C_1$-$C_4$)-sulfanilamido; thiomorpholino-S,S-dioxide; p-chlorobenzoyl hydrazido; p-chlorobenzylidene hydrazino; nicotinylidene hydrazino loweralkylthioloweralkoxy and loweralkylsulfonylloweralkoxy or —$NR_4$—CO—$R_5$ where $R_4$ is hydrogen or alkyl $C_1$-$C_4$ and $R_5$ is alkyl $C_1$-$C_{11}$, phenyl, 3,4-dichlorophenyl, 4-chloro-3-nitrophenyl, benzyl, mono and dihaloalkyl $C_1$-$C_4$ or 2-phenoxypropionamide; $R_1$ is hydrogen or alkyl $C_1$-$C_4$; $R_2$ and $R_3$ are hydrogen or methyl; and the pharmaceutically acceptable acid addition salts thereof.

2. A method according to claim 1 wherein the compound has the formula:

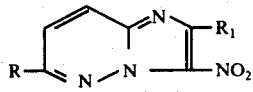

wherein R is hydroxy, mercapto, alkoxy ($C_1$-$C_8$) alkylthio ($C_1$-$C_8$), phthalimidoloweralkoxy, phenylloweralkoxy, lower alkylaminoloweralkoxy, lower alkoxyloweralkoxy, hydroxyloweralkoxy, lower alkenyloxy, halobenzoylloweralkoxy, amino, alkyl ($C_1$-$C_8$) amino, dialkyl ($C_1$-$C_8$) amino, di(hydroxyloweralkyl)amino, hydroxyloweralkylamino, lower alkoxyloweralkylamino, lower alkenylamino, phenylloweralkylamino, pyridylloweralkylamino, cycloalkyl ($C_3$-$C_6$) amino, diloweralkylaminoloweralkylamino, 1-piperidinyl, 1pyrrolidinyl, 4-loweralkyl-1-piperazinyl, 4-lower alkoxyphenyl-1-piperazinyl, morpholino, imidazolyl, 4-carboloweralkoxy-1-piperazinyl, or 4-diloweraminoloweralkyl-1-piperazinyl lower alkylthioloweralkoxy, lower alkylsulfonylloweralkoxy; $R_1$ is hydrogen or loweralkyl and a pharmaceutically acceptable acid addition salf thereof.

3. A method according to claim 1 wherein the compound has the formula:

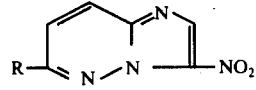

where R is sulfanilamido, alkyl ($C_1$-$C_4$)sulfanilamido, 3-nitro-4-chlorobenzamido, thiomorpholino-S,S-dioxide, p-chlorobenzoyl hydrazido, p-chlorobenzylidene hydrazino, nicotinylidene hydrazino or —$NR_4$—CO—$R_5$ where $R_4$ is hydrogen or alkyl $C_1$-$C_4$ and $R_5$ is alkyl $C_1$-$C_{11}$, phenyl, 4-chloro-3-nitrophenyl, benzyl, mono or dihaloalkyl $C_1$-$C_4$ or 2-phenoxypropionamide and the pharmaceutically acceptable acid addition salts thereof.

4. A method according to claim 2 wherein $R_1$ is hydrogen and R is 4-loweralkyl-1-piperazinyl, amino alkoxy $C_1$-$C_8$, diloweralkylaminoloweralkylamino, hydroxyloweralkylamino or imidazolyl and the pharmaceutically acceptable salts thereof.

5. A method according to claim 3 wherein R is —$NR_4$—CO—$R_5$; $R_4$ is hydrogen or methyl and $R_5$ is alkyl $C_1$-$C_{11}$, phenyl, 4-chloro-3-nitrophenyl, benzyl, dichloromethyl or 3-phenoxypropionamide and the pharmaceutically acceptable salts thereof.

6. A method according to claim 1 wherein the compound is 3-nitro-6-propoxyimidazo[1,2-b]pyridazine.

7. A method of controlling and preventing foot rot and liver abscesses in ruminant animals which comprises administering to the ruminant animals an oral ration containing from about 25 parts to about 500 parts per million of ration of a 6-substituted 3-nitroimidazo[1,2-b]pyridazine according to claim 1.

* * * * *